US00PP09176P

United States Patent [19]

Kustigian

[11] Patent Number: Plant 9,176

[45] Date of Patent: Jun. 20, 1995

[54] CHRYSANTHEMUM PLANT NAMED 'YELLOW GINGER'

[76] Inventor: Robert B. Kustigian, 1387 Main St., Worcester, Mass. 01603

[21] Appl. No.: 181,382

[22] Filed: Jan. 11, 1994

[51] Int. Cl.[6] ..... A01H 5/00
[52] U.S. Cl. ..... Plt./78
[58] Field of Search ..... Plt. 82.2, 82.3, 78, Plt. 79

[56] References Cited

U.S. PATENT DOCUMENTS

| | | | |
|---|---|---|---|
| P.P. 6,403 | 11/1988 | Mack et al. | Plt./78 |
| P.P. 6,404 | 11/1988 | Mack et al. | Plt./78 |
| P.P. 6,621 | 2/1989 | Mack et al. | Plt./78 |
| P.P. 7,725 | 11/1991 | Fuess | Plt./78 |

*Primary Examiner*—Howard J. Locker
*Attorney, Agent, or Firm*—Blodgett & Blodgett; Timothy H. Joyce

[57] ABSTRACT

A Chrysanthemum plant named Yellow Ginger particularly characterized by its flat capitulum form; decorative capitulum type; complete and uniform yellow ray floret color; diameter across face of capitulum of up to 5.5 cm at maturity; small plant height with spreading and prolific branching patter; uniform seven week photoperiodic flowering response to short days in photoperiodic controlled flowering programs; resistance to fade during bloom; average natural season flower date of mid-March to November in New England; and slightly earlier and longer lasting bloom as contrasted to Ginger.

3 Drawing Sheets

The present invention comprises a new and distinct cultivar of Chrysanthemum plant, botanically known as *Chrysanthemum morifolium,* Ramat. and referred to by the cultivar name Yellow Ginger which is a sport of the cultivar Ginger which is described in U.S. Plant Pat. No. 6,403. Yellow Ginger is a naturally occurring branch sport of Ginger.

Ginger was originated from a cross made by Grace H. Mack in a controlled breeding program in New Canaan, Conn., in 1981 and identified by seedling identification No. 82M18017. The parents of Ginger were both unnamed seedlings. Ginger was discovered and selected as one flowering plant within the progeny of the stated cross by Cornelius P. VandenBerg, in September 1982, in a controlled environment in Salinas, Calif. The first act of asexual reproduction of Ginger was accomplished when vegetative cuttings were taken from the initial selection in December 1982 in a controlled environment in Salinas, Calif., by technicians working under formulations established and supervised by Cornelius P. VandenBerg.

The present invention Yellow Ginger was originated and selected from a Ginger flower block taken from the parent cultivar of the Prophets® series by Yoder Brothers, Inc., of Barberton, Ohio. The Yoder Ginger garden mum series refers to U.S. Plant Pat. No. 6,403 as the original parent source of its flower block.

Yellow Ginger has been successfully asexually reproduced by Robert Kustigian from branch cuttings in a controlled greenhouse environment in North Oxford, Mass.

Horticultural examination of controlled flowerings of successive plantings has shown that the unique combination of characteristics as herein disclosed for Yellow Ginger are firmly fixed and are retained through successive generations of asexual reproduction.

Yellow Ginger has not been observed under all possible environmental conditions. The phenotype may vary significantly with variations in environment such as temperature, light intensity, and day length.

The following observations, measurements and comparisons describe plants grown in a controlled area in North Oxford, Mass. Rooted cuttings were established in soil and maintained indoors in greenhouses under simulated conditions of natural temperature and daylight. Single pinching was practiced with all branches and buds retained. Suggested flowering in the northern, eastern, north eastern (New England) and western United States is from January through November, in southern states, year round (January through December) and in Florida, December through April.

The new cultivar, Yellow Ginger, is similar in many respects to Ginger; having the same characteristics of Ginger of:

(1) Flat capitulum form.
(2) Decorative capitulum type.
(3) Diameter across face of capitulum up to 5.5 cm at maturity.
(4) Short plant height.
(5) Spreading and prolific branching pattern.
(6) Uniform seven week photoperiodic flowering response.
(7) Sturdy stem and habit.
(8) Durability in shipment.
(9) Resistance to sun scald.
(10) Resistance to shatter.
(11) Absence of disc florets.

The new cultivar is distinguished from Ginger by the following characteristics:

(1) Complete and uniform yellow ray floret color.
(2) Slightly earlier bloom than Ginger. Ginger's natural bloom time being August 26 in Salinas, Calif. and around the last week in September in New England. Yellow Ginger's bloom time is the first week of September in New England.
(3) Slightly longer length of bloom than Ginger.
(4) Resistance to floret color fade.

The accompanying photographic drawings show typical inflorescence and leaf characteristics of Yellow Ginger with the colors being as nearly true as possible with illustrations of this type.

Sheet 1 is a color photograph of Yellow Ginger grown as a pinched spray pot mum.

Sheet 2 is a color photograph of three views of the inflorescence of Yellow Ginger.

Sheet 3 is a color photograph comparing the flowers of Yellow Ginger and Ginger.

Of the commercial cultivars known to the inventors, the most similar in comparison to Yellow Ginger is Ginger, disclosed in U.S. Plant Pat. No. 6,403. Reference is made to the attached Botanical Classification which compares certain characteristics of Yellow Ginger to the same characteristics of Ginger.

Other varieties, such as Legend (U.S. Plant Pat. No. 6,404) and Target (U.S. Plant Pat. No. 6,621) have similar characteristics to Yellow Ginger. However, Legend is noticeably different due to its pompon petallage style and Target has a dark golden center. Most importantly, both flower types lack the complete and uniform yellow floret of Yellow Ginger. Yellow Ginger has no contrasting bronze-red center of capitulum as in Ginger, or dark golden center petallage as in Target.

In the following description, color references are made to the Royal Horticultural Society Colour Chart. Color values given are those closest to the actual color. The color values were determined on plant material grown in Worcester, Mass., on Dec. 30, 1993.

BOTANICAL CLASSIFICATION
*Chrysanthemum morifolium*

| Flower name: | Yellow Ginger | Ginger |
|---|---|---|
| Bloom: | | |
| Size | ¼" bud | ¼" bud |
| Fully Expanded | 2½" (5.5 cm at maturity | 2½" (5.5 cm at maturity |
| Borne | Terminal on disbudded branches | Terminal on disbudded branches |
| Stems | Strong | Strong |
| Form Type (Capitulum) | Flat Decorative (spray pot and garden mum) | Flat Decorative (spray pot and garden mum |
| Permanence | 16–18 days (resists fade) | 10–12 days (quick fade) |
| Color (Corolla of ray florets): | | |
| Center of Flower | Yellow 12A to 14A | Yellow 12A to 14A with bronze red center (169A to 169C) |
| Base of Petals | Yellow 12A to 14A | Two tone bronze |

-continued

BOTANICAL CLASSIFICATION
*Chrysanthemum morifolium*

| Flower name: | Yellow Ginger | Ginger |
|---|---|---|
| | | 169A to 169C |
| Inside of Petals | Yellow 12A to 14A | Yellow 12A to 14A with bronze on tips |
| Reverse of Petals | Yellow 12A to 14A | Yellow 12A to 14A |
| Tonality from a distance of about 3 meters | Yellow | Bronze |
| Discoloration | non-oxidation | oxidation in sun |
| Petals: | | |
| Texture and shape | Smooth,flat oblong | Smooth,flat oblong |
| Appearance and form | Not open at base, shallow keel | Not open at base, shallow keel |
| Arrangement | Fully decorative | Fully decorative |
| Persistence | Resist shatter | Resist shatter |
| Reproductive Organs: | | |
| Androecium | Not present | Not present |
| Pollen | Not present | Not present |
| Gynoecium | Present on ray florets | Present on ray florets |
| Plant: | | |
| Form | Herbaceous | Herbaceous |
| Growth | Upright | Upright |
| Height | Short | Short |
| Spread | 15–16" as a pinched plant (spreading and prolific) | 15–16" as a pinched plant (spreading and prolific) |
| Foliage: | | |
| Top Side | 137A to 137B | 137A to 137B |
| Underside | 137B to 137C | 137B to 137C |
| Quantity | Numerous | Numerous |
| Shape | Spatulate lobed | Spatulated lobed |
| Texture | Smooth | Smooth |
| Ribs and veins | Slight prominence | Slight prominence |
| Edge | Indented | Indented |
| Serration | Slightly serrated | Slightly serrated |
| Size | 3" long × 1.5" wide | 3" long × 1.5" wide |

We claim:

1. A new and distinct Chrysanthemum plant named Yellow Ginger, as described and illustrated, and particularly characterized as to uniqueness by the combined characteristics of flat capitulum form; decorative capitulum type, complete and uniform yellow ray floret, capitulum, and corolla color, diameter across face of capitulum of up to 5.5 cm at maturity; short plant height with spreading and prolific branching pattern; uniform seven week photoperiodic flowering response to short days in photoperiodic controlled flowering programs, resistance to fade during bloom; average natural season flower date of Mid-March to November in New England.

* * * * *

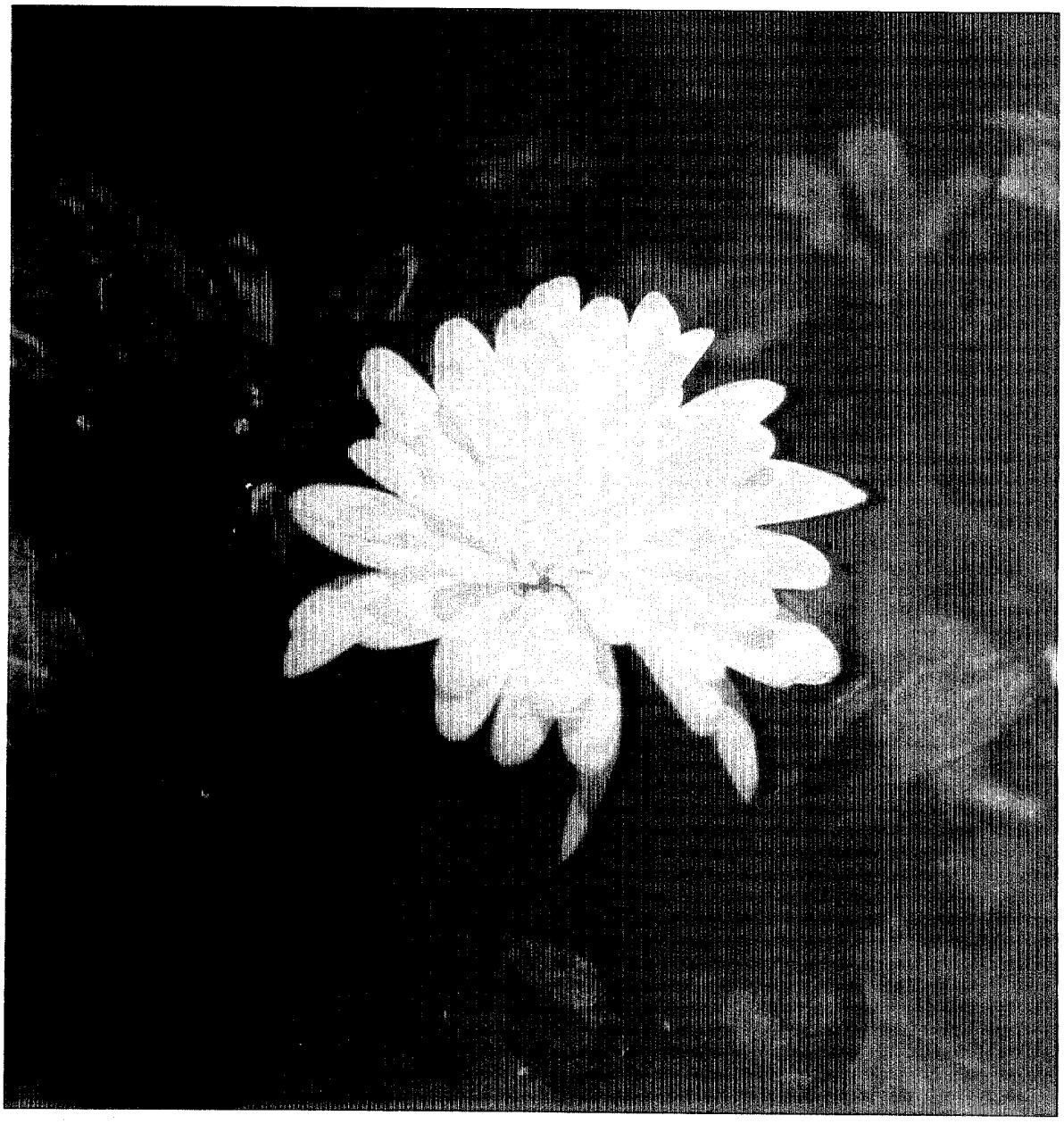
SHEET 1

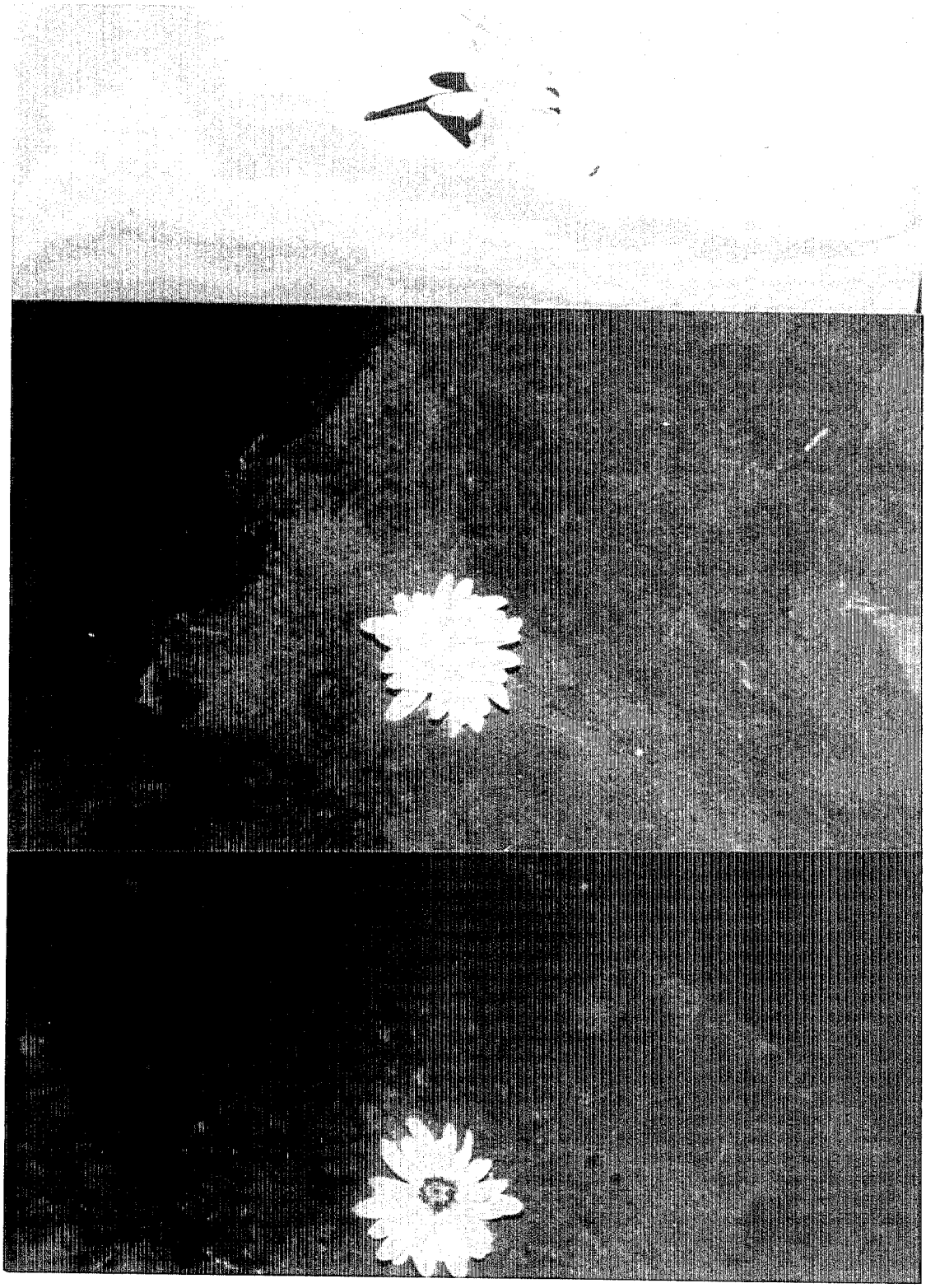
SHEET 2

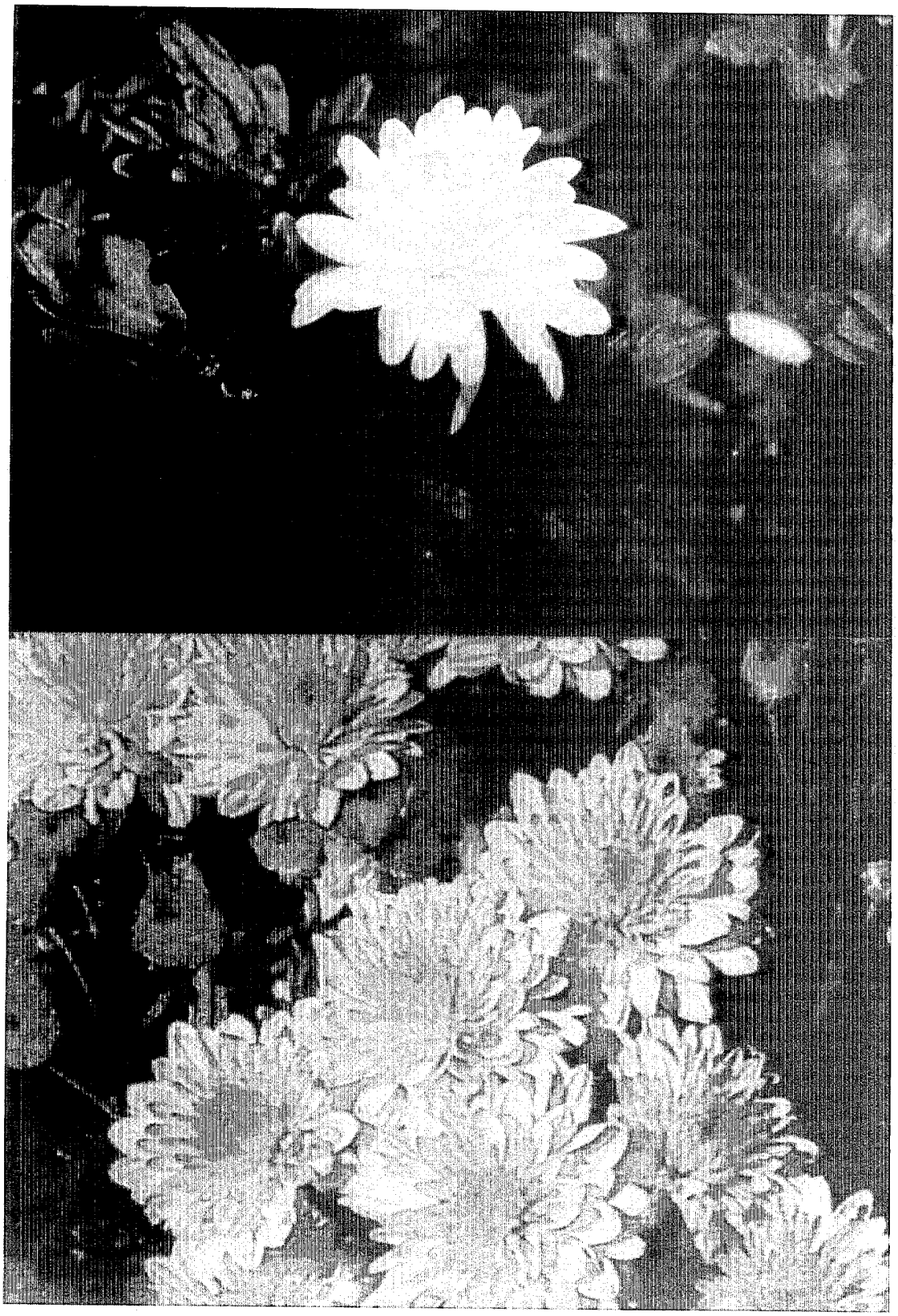
SHEET 3